United States Patent [19]

Barda

[11] 4,404,361
[45] Sep. 13, 1983

[54] FLAME RETARDANT FOR POLYMERIC COMPOSITIONS

[75] Inventor: Henry J. Barda, North Brunswick, N.J.

[73] Assignee: Saytech, Inc., Sayreville, N.J.

[21] Appl. No.: 338,531

[22] Filed: Jan. 11, 1982

[51] Int. Cl.$^3$ .................... C07D 403/12; C08G 73/06
[52] U.S. Cl. ...................................... 528/342; 524/94; 524/411; 524/412; 525/180; 525/435; 548/451; 548/461
[58] Field of Search ........................ 260/326 N, 501.1; 524/94; 528/423, 424, 342; 548/451, 461

[56] References Cited

U.S. PATENT DOCUMENTS

| | | | |
|---|---|---|---|
| 2,330,524 | 9/1943 | Shields | 260/501.1 |
| 2,596,674 | 5/1952 | Gaudin | 260/501.1 |
| 3,455,950 | 7/1969 | Cyba et al. | 260/326 |
| 3,574,230 | 4/1971 | Cyba | 260/326 |
| 3,748,340 | 7/1973 | Hayes et al. | 260/326 C |
| 3,873,567 | 3/1975 | Cyba | 260/326 C |
| 4,001,179 | 1/1977 | Richter et al. | 524/94 |
| 4,087,441 | 5/1978 | Lee | 260/326 N |
| 4,092,345 | 5/1978 | Wolford et al. | 260/501.16 |

FOREIGN PATENT DOCUMENTS 961589  1/1975  Canada .................... 400/55

Primary Examiner—John Kight, III
Assistant Examiner—R. A. White
Attorney, Agent, or Firm—D. L. Johnson; John F. Sieberth; Teresa M. Stanek

[57] ABSTRACT

An additive flame retardant bisimide containing halogen atoms and ammonium acid tetrahalophthalate, e.g. N,N'-bis(2-ethylene tetrabromophthalimide) ammonium acid tetrabromophthalate. These compounds are useful in a variety of polymeric compositions and demonstrate increased thermal stability. They also foam on decomposition with the evolution of gas thus readily lending themselves to the preparation of flame retardant coatings.

13 Claims, No Drawings

FLAME RETARDANT FOR POLYMERIC COMPOSITIONS

BACKGROUND OF THE INVENTION

1. Field of the Invention

This invention relates to a novel flame retardant additive for use in polymeric compositions. More particularly, this invention relates to an additive having amine salt and imide functions. Specifically, this invention relates to novel compounds consisting of bisimides containing halogen atoms and ammonium acid tetrahalophthalate.

2. Description of the Prior Art

A variety of compounds exist which impart satisfactory flame resistance, smoke suppression and self-extinguishing properties to polymeric compositions. U.S. Pat. No. 4,092,345 teaches the use of alkylene diammonium bis-tetrahalophthalates as flame retardants. A variety of other U.S. patents claim fire retardant compounds based on bisimides, dicarboxylic acids or dicarboximides.

U.S. Pat. No. 3,455,950 describes the use and preparation of N,N'-bisimides of polyhalosubstituted polyhydropolycyclicdicarboxylic acids. U.S. Pat. No. 3,748,340 relates to the bisimides of the above-mentioned acids. U.S. Pat. No. 3,574,230 describes haloaryl imides of polyhalopolyhydropolycyclicdicarboxylic acids.

U.S. Pat. No. 3,873,567 claims N-substituted polybromoaromatic ortho-dicarboximides. Canadian Pat. No. 961,589 relates to compositions comprising macromolecular inflammable materials, such as polymers, and a flame retarding amount of a broad range of bisimides.

It has now been discovered that bisimides containing halogen atoms and ammonium acid tetrahalophthalate groups are useful as flame retardants in polymeric compositions. These new compounds have increased thermal stability over prior art compounds, such as alkylene diammonium bis-tetrahalophthalates. The new compounds contain both ammonium salt and imide functions and foam on decomposition with the evolution of gas. This foaming effect is favorable in the preparation of flame retardant coatings.

SUMMARY OF THE INVENTION

According to the present invention, a halogen-containing compound having an amine salt and an imide bridge is an effective flame retardant in polymeric compositions.

DESCRIPTION OF THE PREFERRED EMBODIMENTS

A preferred embodiment of the invention is an additive flame retardant compound comprising a halogen-containing bisimide having the formula:

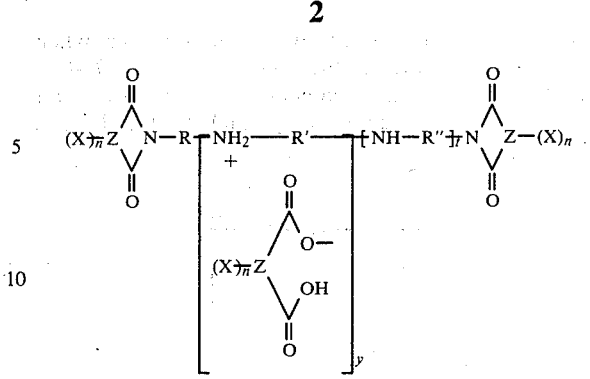

wherein Z is a hydrocarbon group having the valence $n+2$ and is selected from the group consisting of benzene groups, naphthalene groups and alicyclic hydrocarbon groups containing 5-10 carbon atoms, X is selected from the group consisting of bromine and chlorine, n is an integer from 1-6, R, R' and R" are divalent hydrocarbon groups independently selected from the group consisting of aliphatic hydrocarbon groups and alicyclic hydrocarbon groups containing 2-12 carbon atoms, y is an integer from 1-50 and t is an integer from 0-49. These compounds are useful flame retardants in polymeric compositions.

Z is preferably a benzene group. However, some examples of alicyclic hydrocarbon groups which may be represented by Z include cyclopentane, cyclohexane, norbornane and 5-norbornene.

X may be chlorine, bromine or any combination of chlorine and bromine. Preferably, X is bromine. Generally, the greater the number of bromine atoms present in a compound, the greater the flame retardant efficiency on a weight basis. Accordingly, n is preferably 4 when Z is a benzene group and n is preferably 6 when Z is a 5,6-norbornene group or a naphthalene group.

R and the repeating units R' and R" are divalent hydrocarbon groups independently selected from the group consisting of aliphatic hydrocarbon groups and alicyclic hydrocarbon groups containing 2-12 carbon atoms. The value of y dictates the number of times the unit

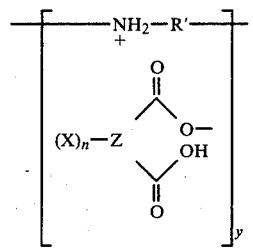

is repeated. y must be at least one so there is at least one secondary ammonium ion and one carboxylate ion present in the connecting bridge between the two nitrogen atoms of the imide groups. For each increasing integer value of y, R' is reselected from the group consisting of aliphatic hydrocarbon groups and alicyclic hydrocarbon groups containing 2-12 carbon atoms.

The value of t dictates the number of times the unit $+NH-R"+$ is repeated. This unit is optional. The symbol t indicates the number of times R" is reselected from the group consisting of aliphatic and alicyclic hydrocarbons containing 2-12 carbon atoms. t is an integer from 0-49. Preferably, t is 0. However, when the value of t indicates the presence of 1 to 49 $-\!\!+\!\!N\!\!-\!\!H\!\!-\!\!R''\!\!+\!\!-$ units in the compound, these units are not limited to certain sections of the imide bridge. That is, the two units

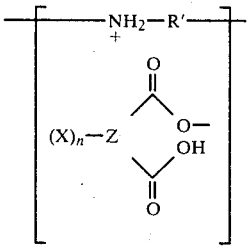

and $-\!\!+\!\!NH\!\!-\!\!R''\!\!+\!\!-$ may be randomly dispersed in the connecting bridge between the two nitrogen atoms of the imide groups. The number of times these units are present in the connecting bridge are dictated by the symbols y and t, respectively.

R, R' and R" represent divalent aliphatic hydrocarbon groups containing 2-12 carbon atoms such as ethylene, trimethylene, methylethylene, tetramethylene, ethylethylene, 2-methyltrimethylene, 2,2-dimethyltrimethylene, 1,4-cyclohexylene, 2,5-cyclohexadien-1,4-xylene, and the like. Alicyclic hydrocarbon groups include cyclopropane, cyclopentane, cyclohexane, and the like. Preferably, R and the repeating units R' and R" each ethylene, —CH$_2$CH$_2$—, y is preferably 1 and t is preferably 0.

Alternatively, Z is 5,6-norbornene and the carbonyl groups are attached at the 2 and 3 positions. X is chlorine, n is 6, R and R' are each ethylene, y is 1 and t is 0.

A preferred method of making the compounds of the present invention involves reacting a halogen-containing dicarboxylic anhydride with an alkylene polyamine having at least three amine groups of which two are primary.

A mixture of water and propionic acid is placed in a reaction flask and heated to a temperature of about 25° C. to about 150° C. The weight ratio of water to propionic acid should be in the range of about 1:9 to about 9:1.

A solution of water and a polyamine is prepared. The polyamine has the structure:

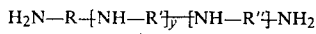

wherein R, R' and R" are divalent hydrocarbon groups independently selected from the group consisting of aliphatic hydrocarbon groups containing 2-12 carbon atoms, y is an integer from 1-50 and t is an integer from 0-49. The preferred polyamines are the alkylene polyamines such as diethylene triamine, triethylene tetramine, tetraethylene pentamine, pentaethylene hexamine, dipropylene triamine, tripropylene tetramine, and the like.

A separate solution of halogen-containing dicarboxylic anhydride is prepared. The combined amount of water used in this reaction should be sufficient to hydrolyze the halogen-containing dicarboxylic anhydride. Halogen-containing dicarboxylic anhydride compounds used in preparing the compounds of the present invention have the structure:

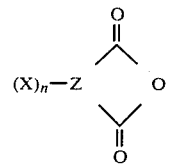

wherein Z is a hydrocarbon group having the valence n+2 and is selected from the group consisting of benzene groups, naphthalene groups and alicyclic hydrocarbon groups containing 5-10 carbon atoms, X is selected from the group consisting of bromine and chlorine and n is an integer from 1-6. Typical halogen-containing anhydrides include:
  3-chlorophthalic anhydride,
  4-bromophthalic anhydride,
  3,6-dibromophthalic anhydride,
  tetrabromophthalic anhydride,
  tetrachlorophthalic anhydride,
  1,4,5,6,7,7-hexachlorobicyclo(2.2.1)-5-heptene-2,3-dicarboxylic anhydride.
  1,4,5,6,7,7-hexachloro-2-methylbicyclo(2.2.1)-5-heptene-2,3-dicarboxylic anhydride,
  1,4,5,6,7,7-hexachlorobicyclo(2.2.1)-5-heptene-2-acetic-2-carboxylic anhydride
  5,6,7,8,9,9-hexachloro-1,2,3,4,4a,5,8,8a-octahydro-5,8-methano-2,3-naphthalene dicarboxylic anhydride,
  1,2,3,4,5,6,7-octachloro-3,6-methano-1,2,3,6-tetrahydrophthalic anhydride,
  1,4-dichloro-2,3-naphthalene-dicarboxylic anhydride and
  1,4-dibromo-2,3-naphthalene-dicarboxylic anhydride.

Mixtures of any of the above anhydrides may also be employed as well as mixtures of the above anhydrides and nonhalogenated anhydrides. Preferably, the halogenated dicarboxylic anhydride is tetrabromophthalic anhydride.

The amount of dicarboxylic anhydride per equivalent of amine can vary over a wide range. The number of repeating units, indicated by the symbols y and t in the connecting bridge between the two imide groups, dictate the desired ratio of dicarboxylic anhydride to equivalent of amine. For example, the amine reactant contains two primary amine groups and y+t secondary amine groups. Hence, each mole of the amine reactant will require y+2 moles of dicarboxylic anhydride. One mole of diethylene triamine is three equivalents of amine, two of which are primary. Since there is only one secondary amine group, it must be converted to an ammonium salt so y is 1, t is zero and three moles of dicarboxylic anhydride are required. In the case of tetraethylene pentamine y can be 1-4 and t can be 0-3. Hence, from 3-5 moles of dicarboxylic anhydride can be used per mole of tetraethylene pentamine.

It is important, however, that at least three moles of dicarboxylic anhydride are used per polyamine. Two moles of dicarboxylic anhydride form imides with the terminal nitrogens of the polyamine and at least one ammonium ion/carboxylate ion set is present in the connecting bridge between each of the imide groups.

The polyamine solution and dicarboxylic acid solution are then alternately added in incremental amounts every 5-10 minutes to the reaction flask. Once the entire amount of both solutions is added, the mixture is maintained at about 25° C. to about 150° C. for approximately 1-4 hours. The mixture is then cooled and the precipitate is filtered off, washed and dried. After oven dehydration of the precipitate at about 130° C. to about 250° C. for about 6 hours the product of the invention is obtained.

The halogen-containing bisimides of the present invention are additive flame retardants used in either thermoset or thermoplastic polymer compositions. The thermoset polymers consist of those plastics which when subjected to heat, will normally become infusible or insoluble and as such cannot be remelted. They have elaborately cross-linked three dimensional structures and are used for plastics, elastomers, coatings and adhesives. The following are some of the commonly used compression-molded thermosetting compounds. They are obtained by condensation reactions between formaldehyde and substances such as melamine, phenol and urea. These compounds are melamine formaldehyde, phenol formaldehyde and urea formaldehyde.

In contrast to the thermoset polymers, most thermoplastic polymers can be made to soften and take a new shape by the application of heat and pressure. Thermoplastics consist of long-chain molecules often without any branching (e.g., high density polyethylene). Even if there is branching (e.g., low density polyethylene) the polymer may still be two dimensional. Thermoplastic polymers consist of those plastics which normally are rigid at operating temperatures, but can be remelted and reprocessed. They include polyethylene, polypropylene, polystyrene, polyvinyl chloride, acrylonitrile-butadiene-styrene (ABS), nylon, and the like.

There is no definite upper limit for the amount of total additives to be incorporated in the polymer composition. Ordinarily, additives are used at the lowest level which will provide the desired degree of flame retardance and which will produce the least change in the physical properties of the polymer composition. The halogen-containing bisimides of the present invention are unusually efficient. They are normally present in low concentrations. Frequently, they are present in a range of about 0.1-50 weight percent based on the weight on the entire polymer composition. Preferably, they are present in a range of about 1.0-40 weight percent based on the weight of the entire composition.

Flame retardant synergists may also be employed in the thermoset or thermoplastic polymer composition. Common synergists include antimony oxide, zinc oxide, zinc borate, bicumyl peroxide and aliphatic or cycloaliphatic phosphites or thiophosphites. The polymer composition can also have the usual fillers, dyes, pigments, plasticizers, anti-static agents, stabilizing agents, and the like incorporated therein, if desired. These additives are known in the art.

The following example shows the method for making the additives but it is to be understood that the invention is not limited to these specific examples.

EXAMPLE I

A mixture of 163.1 g of water and 81.2 g of propionic acid was charged into a reaction flask. The mixture was heated to 95° C. A solution having a volume of 36 ml was prepared by adding 26.3 g of water to 9.3 g of diethylenetriamine. Additions to the flask are made at seven minute intervals starting with 7 g of tetrabromophthalic anhydride and alternating with 2 ml of the amine solution, for a total of seven additions for each reagent. A total of 49 g (0.106 mole) of tetrabromophthalic anhydride and a total of 3.6 g (0.035 mole) of diethylenetriamine was added. After the last addition, the mixture was maintained at 95° C. for one hour, cooled to room temperature, filtered and the precipitate washed with 50 ml of water, and dried at 70° C. to give 54.0 g of an intermediate. A 10 g sample was oven dehydrated at 180° C. for six hours to obtain 8.8 g of product. This is equivalent to a 91.9% yield of N,N'-bis(2-ethylene tetrabromophthalimide) ammonium acid tetrabromophthalate. The product decomposed with foaming at 235° C. Calculated for $C_{28}H_{11}N_3O_8Br_{12}$: C, 22.78%; H, 0.75%; N, 2.85%; Br 64.96%; Found: C, 22.92%; H, 0.68%; N, 2.79%; Br, 61.25%.

The following table demonstrates the advantage of incorporating the flame retardant of the present invention into the medium impact polystyrene. N,N'-bis(2-ethylene tetrabromophthalimide) ammonium acid tetrabromophthalate was added to a medium impact polystyrene, Shell DP 3037 (a trademark of Shell Chemical Co.). Shell DP 3037 is a high heat, medium impact polystyrene resin with an Izod impact strength of 1.2 ft. lb./inch of notch and a deflection temperature of 192° F. (264 psi). Antimony oxide is a synergist and was used along with the halogenated bisimide of the present invention to provide improved flame retardant properties.

The compositions were prepared in a Brabender plasticorder, fitted with a number 6 roller head having a 60 cc capacity and heated at a stock temperature of 350°-365° F., at 60 rpm for five minutes. The compositions were then compression molded at 400° F. for five minutes into plaques measuring $2'' \times 5'' \times \frac{1}{8}''$. Samples for testing were trimmed to meet the size requirements for Oxygen Index or UL-94 test procedures.

The Oxygen Index Test is defined as the minimal volume fraction of oxygen in a slowly rising gaseous atmosphere that will sustain the candle like burning of a stick of polymer. The higher the Oxygen Index of a molded article, the more flame retardant it is.

The UL-94 vertical burn test is used to classify polymer specimens as V-0, V-1, V-2 and burn. Polymer specimens are held vertically and ignited at the bottom. Classification is based on burn times, the presence or absence of flaming drip and the presence and extent of afterglow.

TABLE I

| EVALUATION IN MEDIUM IMPACT POLYSTYRENE | | | | | |
|---|---|---|---|---|---|
| | I | II | III | IV | V |
| | COMPOSITION (WT.%) | | | | |
| Shell DP 3037 | 100 | 91.4 | 87.2 | 83.0 | 81.1 |
| Flame Retardant from Example | — | 6.6 | 9.8 | 13.0 | 15.2 |
| Antimony Oxide | — | 2.0 | 3.0 | 4.0 | 4.7 |
| % Bromine | 0 | 4 | 6 | 8 | 10 |
| | TEST RESULTS | | | | |
| Oxygen Index | 18.5 | 23.1 | 23.8 | 25.5 | 27.8 |
| UL-94 | burn | burn | V-2 | V-O | V-O |

As indicated by Table 1, as the amount of N,N'-bis(2-ethylene tetrabromophthalimide) ammonium acid tetrabromophthalate and antimony oxide is increased, a noticeable improvement in the flame retardant properties of the medium impact polystyrene results.

I claim:
1. An additive flame retardant halogen-containing bisimide having the formula:

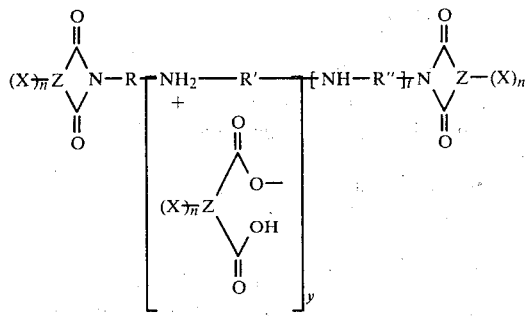

wherein Z is a hydrocarbon group having the valence n+2 and is selected from the group consisting of benzene groups, naphthalene groups and alicyclic hydrocarbon groups containing 5-10 carbon atoms, X is selected from the group consisting of bromine and chlorine, n is an integer from 1-6, R, R' and R" are divalent hydrocarbon groups independently selected from the group consisting of aliphatic hydrocarbon groups and alicyclic hydrocarbon groups containing 2-12 carbon atoms, y is an integer from 1-50 and t is an integer from 0-49.

2. A flame retardant, as recited in claim 1, wherein Z is a benzene group.

3. A flame retardant, as recited in claim 2, wherein X is bromine.

4. A flame retardant, as recited in claim 3, wherein n is 4.

5. A flame retardant, as recited in claim 4, wherein R, R' and R" are each ethylene.

6. A flame retardant, as recited in claim 5, wherein y is 1.

7. A flame retardant, as recited in claim 6, wherein t is 0.

8. A flame retardant, as recited in claim 1, wherein Z is 5,6-norbornene.

9. A flame retardant, as recited in claim 8, wherein X is chlorine.

10. A flame retardant, as recited in claim 9, wherein n is 6.

11. A flame retardant, as recited in claim 10, wherein R and R' are each ethylene.

12. A flame retardant, as recited in claim 11, wherein y is 1.

13. A flame retardant, as recited in claim 12, wherein t is 0.

* * * * *

UNITED STATES PATENT AND TRADEMARK OFFICE
CERTIFICATE OF CORRECTION

PATENT NO. : 4,404,361

DATED : SEPTEMBER 13, 1983

INVENTOR(S) : HENRY J. BARDA

It is certified that error appears in the above-identified patent and that said Letters Patent is hereby corrected as shown below:

Column 3, Line 51, reads "$H_2N - R -[NH - R']_y-[NH - R'']- NH_2$", and should read -- $H_2N - R -[NH - R']_y-[NH - R'']_t- NH_2$ --.

Column 5, Line 4, reads "invention", and should read -- present invention --.

Signed and Sealed this

Third Day of July 1984

[SEAL]

Attest:

GERALD J. MOSSINGHOFF

Attesting Officer

Commissioner of Patents and Trademarks